(12) United States Patent
Inoue et al.

(10) Patent No.: US 7,378,008 B2
(45) Date of Patent: May 27, 2008

(54) LIQUID ELECTROCHEMICAL GAS SENSOR

(75) Inventors: Tomohiro Inoue, Minoo (JP); Yuki Fujimori, Minoo (JP)

(73) Assignee: Figaro Engineering Inc., Minoo-shi, Osaka (JP)

( * ) Notice: Subject to any disclaimer, the term of this patent is extended or adjusted under 35 U.S.C. 154(b) by 614 days.

(21) Appl. No.: 11/026,053

(22) Filed: Jan. 3, 2005

(65) Prior Publication Data

US 2005/0145494 A1 Jul. 7, 2005

Related U.S. Application Data

(63) Continuation of application No. PCT/JP2004/012258, filed on Aug. 26, 2004.

(30) Foreign Application Priority Data

Nov. 14, 2003 (JP) ............................. 2003-384590

(51) Int. Cl.
*G01N 27/413* (2006.01)
(52) U.S. Cl. ................. 204/430; 204/424; 204/432
(58) Field of Classification Search ............... 204/424, 204/430, 431, 432
See application file for complete search history.

(56) References Cited

U.S. PATENT DOCUMENTS

| | | | |
|---|---|---|---|
| 4,036,724 A * | 7/1977 | Binder et al. ............... | 204/432 |
| 4,406,770 A * | 9/1983 | Chan et al. ................. | 204/406 |
| 4,587,003 A | 5/1986 | Tantram et al. | |
| 4,820,386 A | 4/1989 | LaConti et al. | |
| 5,240,893 A | 8/1993 | Witherspoon | |
| 5,302,274 A | 4/1994 | Tomantschger et al. | |
| 5,338,429 A * | 8/1994 | Jolson et al. ............... | 204/415 |
| 5,650,054 A | 7/1997 | Shen et al. | |
| 5,958,200 A | 9/1999 | Kessel | |
| 6,200,443 B1 | 3/2001 | Shen et al. | |

FOREIGN PATENT DOCUMENTS

| JP | 2002-350393 | * 12/2002 |
|---|---|---|
| WO | WO 02/097420 A1 | 12/2002 |

OTHER PUBLICATIONS

Machine translation of JP 2002-350393, Apr. 2002.*

* cited by examiner

*Primary Examiner*—Kaj K Olsen
(74) *Attorney, Agent, or Firm*—Rothwell, Figg, Ernst & Manbeck, P.C.

(57) ABSTRACT

Water is stored in a metal can, and water vapor is supplied to a separator through an opening in a washer. The separator is an alkali metal salt in a sulfonated synthetic resin membrane, and KOH aqueous solution is used as the electrolyte, and the sensing electrode and the counter electrode are Pt—C, and solid proton conductive membranes are placed between the electrodes and the separator.

17 Claims, 13 Drawing Sheets

LIQUID ELECTROCHEMICAL GAS SENSOR

CROSS REFERENCE TO RELATED APPLICATION

This application is a continuation of PCT/JP04/12258 filed Aug. 26, 2004, and designating the U.S.

FIELD OF THE INVENTION

The present invention relates to liquid electrochemical gas sensors.

BACKGROUND OF THE INVENTION

A gas sensor using solid proton conductive membrane is known (Documents 1 and 7). In this gas sensor, a proton conductive membrane is interposed between a pair of electrodes, and water vapor is fed from a water reservoir. After that, the present inventors considered the possibility of applying the structure of the gas sensor using a solid proton conductive membrane to a gas sensor using a liquid electrolyte.

In a gas sensor using a liquid electrolyte, the electrolyte is held in a separator, and the electrolyte is replenished from a reservoir of the electrolyte by means of a wick. As sulfuric acid is used as the electrolyte, a metal housing can not be used. Furthermore, in an atmosphere of high humidity, sulfuric acid will absorb moisture and may overflow from the reservoir.

Document 2 proposes a liquid electrochemical gas sensor using no wick. Here, sulfuric acid is stored in a water reservoir, and sulfuric acid is arranged to absorb moisture when the humidity is high and release moisture when the humidity is low, thus substantially maintaining the humidity at a constant level in the gas sensor. As a result, the electrolyte in the separator is prevented from drying. Document 3 proposes to set a deliquescent salt such as LiCl in a water reservoir so as to substantially keep the humidity at a constant level in the gas sensor. When sulfuric acid or a deliquescent salt is used, however, there is a possibility that in an atmosphere of high temperature and high humidity or the like the liquid electrolyte may overflow from the water reservoir.

Document 4 discloses a separator wherein colloidal silica and PTFE (polytetrafuluoloethylene) are carried on a paper-like glass filter. Here, it is understood that hydrophilic channels for maintaining the liquid electrolyte are provided by colloidal silica, and hydrophobic channels for diffusing gas are provided by PTFE.

Document 5 discloses an O2 sensor using a liquid electrolyte of KOH or H2SO4, and it is reported that the characteristics will drift when KOH is used.

Document 6 discloses a CO sensor using an MgSO4 aqueous solution.

Document 1: WO 02/097420A1
Document 2: WO 01/14864A1
Document 3: U.S. Pat. No. 5,958,200
Document 4: U.S. Pat. No. 4,587,003
Document 5: U.S. Pat. No. 5,240,893
Document 6: U.S. Pat. No. 5,302,274
Document 7: U.S. Pat. No. 6,200,443

DISCLOSURE OF THE INVENTION

Object of the Invention

An object of the invention is to provide a new liquid electrochemical gas sensor using no sulfuric acid.

CONSTRUCTIONS OF THE INVENTION

The liquid electrochemical gas sensor of the present invention is a gas sensor wherein a liquid electrolyte is held in a porous separator, at least a sensing electrode and a counter electrode are connected to said separator, and water vapor is replenished into said separator from a water reservoir, said gas sensor being characterized in that said separator is made of a hydrophilic organic polymer and holds water or an aqueous solution of an alkali metal hydroxide or an aqueous solution of a water soluble salt having no deliquescence.

Preferably, said separator holds an aqueous solution of an alkali metal hydroxide or pure water, and a gas to be detected is a reducing gas.

Preferably, a solid electrolyte membrane is placed between the separator and the sensing electrode.

Preferably, said counter electrode is an oxide or a hydroxide of Mn, Ni, Pb or Zn.

As for the structure of the gas sensor, preferably, a metal can having an opening and a bottom is provided with a narrowing part between the opening and the bottom, a metal washer having an opening is held by said narrowing part, at least said counter electrode, said separator and said sensing electrode are arranged on said metal washer, and water is contained between the metal washer and the bottom of the metal can.

As for the scope of detection, for example, CO in hydrogen or a reducing gas in an inert gas can be detected.

Particularly preferably, the separator is made of an organic polymer containing an alkali metal salt of sulfonic acid group or containing alcoholic hydroxyl group, and besides them, may be used an organic polymer that is made hydrophilic by an alkali metal salt of carboxyl group, an alkali metal salt or an alkaline earth metal salt of hosphonic acid group, or by phenol group, amino group or imido group, or by a derivative of them. It is desirable to replace the hydrogen ion of the hydrophilic group in the polymer with another positive ion, and this is called saponificaton. For saponification, it is desirable to use an alkali metal ion, but an alkali earth ion or an ammonium ion or its derivative may be used.

The present inventors have found that a separator made of an organic polymer, and made hydrophilic by an alkali metal salt of sulfonic acid group or by alcoholic hydroxyl group enables the detection of a reducing gas such as CO or H2, even if the liquid electrolyte is an aqueous solution of an alkali metal hydroxide such as KOH or NaOH, or even if the liquid electrolyte is a simple water such as pure water or demineralized water. When a separator having a high hydrophilicity is filled with water, the separator will exhibit a slight conductivity. This conductivity is deemed to be related to the movement of ions between the electrodes and the liquid electrolyte. It should be noted that pure water and demineralized water are different terms. In the present invention, as the content of the electrolyte is important, pure water is considered to include demineralized water.

The configuration of the separator is a nonwoven fabric, a membrane having minute holes, or a woven fabric, and the basic material is a synthetic resin such as PP (polypropylene), polyamide resin or PTFE resin. In the case of polyamide resin, it is preferable to use a modified polyamide resin wherein NH group is replaced with N-φ (φ denotes a phenyl group) so as to increase its thermal resistance.

According to the present invention, sensitivity to CO or H2 can be attained without the use of sulfuric acid, and accordingly, a metal package can be used, and moreover, sulfuric acid does not overflow even in an atmosphere of high humidity. As for the liquid electrolyte, an alkaline liquid electrolyte such as an alkali metal hydroxide, for example, KOH can be used, and afforded stable sensitivity to CO. As to the liquid electrolyte, simple water such as demineralized water or an aqueous solution of a water soluble salt having no deliquescence such as MgSO4 can be used. The pH of the liquid electrolyte is, for example, 4 or over, and preferably it is 6 or over,ble, and more preferably, is 7 or over.

When sulfuric acid is used as the liquid electrolyte, the oxidation reaction of CO or H2 proceeds easily at the sensing electrode, but when the liquid electrolyte is neutral or alkaline, it is hard to oxidize CO or H2 or the like at the sensing electrode and to cause proton movement in the liquid electrolyte. Hence the gas sensitivity at lower temperatures is low. In contrast to it, when a solid proton conductive membrane or a hydroxyl ion conductive membrane is provided between the sensing electrode and the separator or such membranes are provided between both faces of the separator and the two electrodes, the gas sensitivity at lower temperatures will increase.

When a reducing gas such as CO is to be detected, the product at the sensing electrode is proton. In the case of an alkali metal hydroxide such as potassium hydroxide, the hydroxy ions will move toward the interface of the sensing electrode and the electrolyte to neutralize protons that are injected from the sensing electrode into the electrolyte, and the following reaction (1) will proceed at the counter electrode.

$$2H_2O+O_2+4e^- \rightarrow OH^- \qquad (1)$$

Both the sensing electrode and the counter electrode may be a catalytic electrode of Pt, Pt—RuO2, Pd, Au, a metal oxide, etc. However, if the counter electrode is an oxide or a hydroxide of Mn, Ni, Pb or Zn, it is more advantageous in terms of cost. At the counter electrode of an oxide or an hydroxide, a reducing gas can be detected even in an atmosphere lacking oxygen. Moreover, in the gas sensor according to the present invention, since the sensitivity to CO is higher than that to hydrogen, the gas sensor can detect CO in hydrogen for fuel cells.

According to the present invention, the sensitivity can be attained by simply moistening the separator by means of water vapor without replenishing the separator with a liquid electrolyte by means of a wick. Accordingly, as to the structure of the gas sensor, for example, a metal can having an opening and a bottom is provided with a narrowing part between the opening and the bottom, a metal washer having an opening is held by said narrowing part, at least said counter electrode and said separator and said sensing electrode are arranged on said metal washer, and water is contained between the metal washer and the bottom of the metal can. The water may be liquid water or gelated water.

The gases to be detected are reducing gases such as CO, hydrogen alcohol, aldehyde, hydrogen sulfide or ammonia. CO in hydrogen or a reducing gas in an inert gas can also be detected.

ADVANTAGES IN THE INVENTION

The present invention has the following advantages:
(1) As sulfuric acid is not used for the liquid electrolyte, a metal can be used for the package, and no sulfuric acid will overflow in an atmosphere of high humidity.
(2) An alkaline liquid electrolyte such as KOH aqueous solution or a neutral liquid electrolyte such as pure water can be used.

BRIEF DESCRIPTION OF THE SYMBOLS

| 2 | | liquid electrochemical gas sensor |
|---|---|---|
| 4 | | sensor |
| 6 | | separator |
| 8 | | sensing electrode |
| 10 | | counter electrode |
| 12 | | hydrophilic conductive membrane |
| 14 | | washer |
| 16 | | water vapor introducing hole |
| 18 | | diffusion control plate |
| 20 | | diffusion control hole |
| 22 | | cap |
| 23 | | bottom plate |
| 24, 26 | | opening |
| 25 | | filter |
| 28 | | metal can |
| 30 | | water |
| 32 | | narrowing part |
| 34 | | adhesive ring |
| 36 | | sealing material |
| 38 | | electron conductive electrode |
| 40 | | solid electrolyte membrane |
| 42 | | proton-electron mixed conductive electrode |
| 50 | | hydrogen tube |
| 51 | | valve |
| 52 | | test room |
| 53 | | suction pump |

EMBODIMENTS

In the following, the best embodiment of the present invention will be described.

Embodiments

Figure 1:
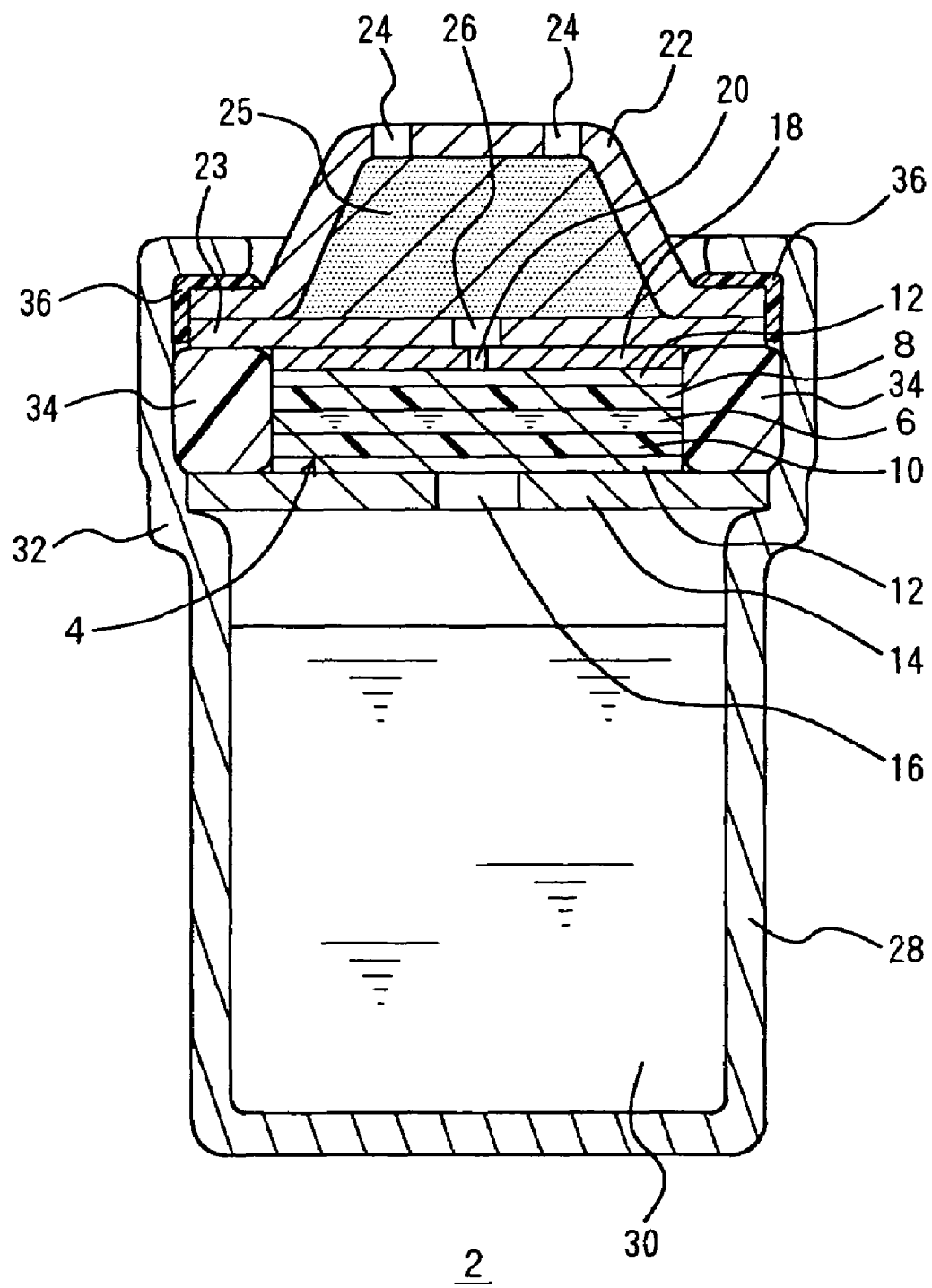
FIG. 1 is a sectional view of the liquid electrochemical gas sensor of an embodiment.

FIG. 1 through FIG. 24 illustrate the embodiment and its modifications. In the embodiment, one with a sulfonated separator is described. However, a carboxylated separator or a separator containing alcoholic hydroxyl group may be used. It should be noted that sulfonic acid group is present in an alkali metal salt of sulfonic acid. In FIG. 1, 2 denotes a liquid electrochemical gas sensor, 4 denotes a sensor, and a sensing electrode 8 and a counter electrode 10 are provided on the face and the back of the separator 6, respectively. The separator 6 is porous and holds a liquid electrolyte, and for example, its thickness is about 0.1 mm and the diameter is about from 5 to 20 mm. The separator 6 comprises, for example, a woven fabric or an unwoven fabric of a synthetic fiber, and is made hydrophilic by, for example, sulfonation or introduction of alcoholic hydroxyl group. The embodiment will be described by taking sulfonation as an example.

Let us assume that the organic polymer of the separator comprises an organic polymer of $(A-SO_3X)_n-(B)_m$ and an organic polymer of $R_p$. A, B and R denote monomers, respectively, n denotes an integer that is not less than 1. m and p denote integers that are not less than 0, and X is, for example, an alkali metal ion. For example, let us assume the organic polymer is a copolymer of $-(A-SO_3X)-$ and $-(B)-$. Then, p is 0, and $n/(n+m)$ is preferably, for example, from $5 \times 10^{-4}$ to $4 \times 10^{-2}$. It should be noted that the indication $(A-SO_3X)_n-(B)_m$ does not mean that n blocks of $(A-SO_3X)$ continue and m blocks of B continue. It means that the ratio of the block $(A-SO_3X)$ and the block B is n: m. When the organic polymer of the separator is a mixture of $(A-SO_3X)_n-(B)_m$ and another organic polymer $R_p$, preferably, $n/(n+m+p)$ is from $5 \times 10^{-4}$ to $4 \times 10^{-2}$. $n/(n+m)$ (when R component is not present) or $n/(n+m+p)$ (when R component is present) is particularly preferably from $5 \times 10^{-3}$ to $1.5 \times 10^{-2}$.

As for the degree of sulfonation, in the case of a nonwoven cloth wherein polyamide fiber is bonded by sulfonated SBR (styrene butadiene rubber), for example, said $n/(n+m+p)$ is about 0.01, and when SBR only is considered, $n/(n+m)$ is about 0.05. In the case of a porous membrane of PP (polypropylene), p is, for example, 0, and $n/(n+m+p)$ is, for example, from about $5 \times 10^{-4}$ to $4 \times 10^{-2}$. For both the polyamide separator and the PP separator, $n/(n+m+p)$ is, for example, $5 \times 10^{-4}$ to $4 \times 10^{-2}$, and preferably, from about $5 \times 10^{-3}$ to $1.5 \times 10^{-2}$.

As a comparative example for the separator 6, a non-woven cloth of polyamide resin using a nonsulfonated SBR binding agent, being treated with a surface-active agent (unknown material), (brand name: WO-DO of MITSUBISHI PAPER MILLS LIMITED) was used. As the embodiment, the nonwoven cloth of polyamide resin with a sulfonated SBR binding agent (polyamide separator, $n/(n+m+p)$ is 0.01, a product of MITSUBISHI PAPER MILLS LIMITED) was used. As another embodiment, a porous membrane of PP (polypropylene), which was sulfonated so that $n/(n+m)$ was 0.01 (PP separator, brand name SFLD50S of NIPPON KODOSHI CORPORATION) was used. As the value of $n/(n+m)$, the degree of sulfonation is so low, this product can not be regarded as a proton conductor. As for ordinary proton conductors, the value of $n/(n+m)$ is 0.12 in Nafion membrane (Nafion is a registered trademark of DuPont), and the value in X Membrane (X Membrane is a registered trademark of Dow) is from 0.14 to 0.09. As shown in Table 1, the conductivity of the separator itself is low or about $1/1000$ of that of an ordinary proton conductive membrane.

Liquid electrolytes were held in the PP separator and the polyamide separator (diameter: 10 mm), pH was measured with pH test paper, and the resistance between the face and the back was measured. The results are shown in Table 1. The separators were neutral even when they were sulfonated, but they exhibited conductivity even for pure water. The sulfonic acid group of the separators are saponificated by an alkali metal ion such as $Na^+$ ion, or by ammonium ion, in particular, by an alkali metal ion, $Na^+$ ion, etc. may be dissolved out in pure water, but their concentration is not higher than $1/100$ M. When KOH or the like is used, a portion of that may be changed into KHCO3 or K2CO3. It, therefore, is desirable that the electrolyte is an alkaline aqueous solution containing alkali metal ion of 3 M or under or pure water.

TABLE 1

Physical Properties of the Separators

| | pH | | Resistance |
|---|---|---|---|
| | Polyamide separator | PP separator | Polyamide separator |
| Dry state | — | — | ∞ |
| Pure water | 7 | 7 | 6 kΩ |
| 0.1 M KOH | 13 | 13 | 500 Ω |
| 1 M KOH | 14 | 14 | 50 Ω |

The sensing electrode 8 comprises, for example, a mixture of carbon black supporting Pt and PTFE (polytetrafluoroethylene) binder. In place of Pt, an appropriate electrode catalyst such as Pt—RuO2 or Pd may be used. The counter electrode 10 is an electrode having a similar composition to that of the sensing electrode 8. 12 denotes a hydrophobic conductive membrane, 14 denotes a metal washer such as SUS, 16 denotes a water vapor introducing hole of which diameter is, for example, from about 1 to 3 mm. 18 denotes a diffusion control plate that is made of a metal thin plate such as SUS, of which thickness is about 100 μm, and it is provided with a diffusion control hole 20 of which diameter is about 0.1 mm. By providing the thin diffusion control plate 18 with a diffusion control hole 20, the hole diameter of the diffusion control hole 20 can be made constant, and in turn, dispersion between the gas sensors can be minimized. 22 denotes a metal cap, 23 denotes a bottom plate thereof, 24 and 26 denote openings for gas introduction, and 25 denotes a filter that uses activated carbon, silica gel, zeolite, etc.

28 denotes a metal can of, for example, SUS, and liquid water 30 such as pure water is stored in the lower part of the metal can. Gelated water may be stored therein. 32 denotes a narrowing part, and said washer 14 is supported on the narrowing part. 34 denotes an adhesive ring comprising an adhesive urethane elastomer, etc., and seals the circumference of the sensor 4 to prevent water from entering from the sides of the sensor body 4. 36 denotes an insulative sealing material, and it may be a sealing tape. The sealing material 36 insulates and seals the gap between the metal can 28 and the cap 22, and in turn, prevents gas from entering through this gap. The upper portion of the metal can 28 is reduced to grip the cap 22. As a result, the sensing electrode 8 and the cap 22 are connected conductively, and the counter electrode 10 and the metal can 28 are connected conductively, and in turn, water leakage and gas penetration through any part other than the diffusion control hole 20 are prevented. When liquid water reaches, through the water vapor introducing hole 16, the hydrophobic conductive membrane 12, liquid water will be blocked by the hydrophobic conductive membrane 12.

Figure 2:
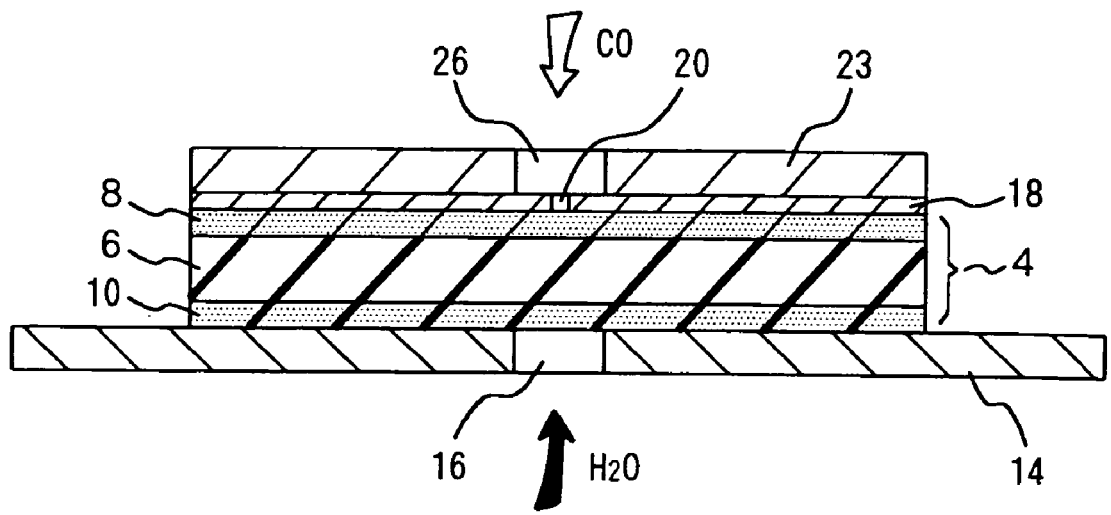
FIG. 2 is a sectional view illustrating the sensor and its periphery of the liquid electrochemical gas sensor of the embodiment.
Figure 3:
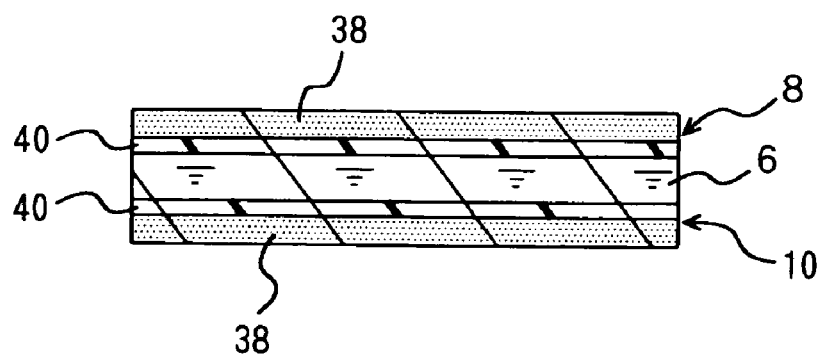
FIG. 3 is a sectional view illustrating the sensor and its periphery of the liquid electrochemical gas sensor of the embodiment.
Figure 4:
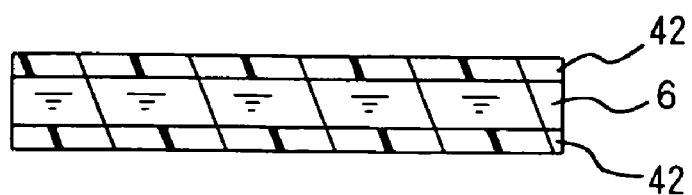
FIG. 4 is a sectional view illustrating the sensor and its periphery of the liquid electrochemical gas sensor of a modification.

FIG. 2 illustrates the supplies of water vapor and CO to be detected,

To attain a sensitivity to CO or H2 at room temperature, it is preferable to make a solid electrolyte contact the electrodes 8 and 10. In FIG. 3, a solid electrolyte membrane 40 comprising a polymer proton conductor or a solid hydroxyl ion conductor or the like, wherein a basic group such as pyridine is introduced into a side chain, is arranged between a electron conductive electrode 38 such as Pt—C-PTFE and the separator 6. In the embodiment, the structure of FIG. 3 was adopted, and a polymer proton conductive membrane was used. As shown in FIG. 4, Pt—C-PTFE or the like may be mixed with a polymer proton conductor or a solid hydroxyl ion conductor to provide an ion-electron mixed conductive electrode 42. When a solid electrolyte is added to the electrodes 8, 10, or when the solid electrolyte membrane 40 is provided, electrode reactions of CO and the like will become easier, and a sensitivity to CO or the like can be attained without using sulfuric acid and even at low temperatures such as −10° C. In the embodiment, a sensor having two electrodes, namely, the sensing electrode and the counter electrode, is used. However, in addition to them, a reference electrode may be provided.

The counter electrode 10 may comprise an oxidizing agent (active material) such as a metal oxide or a metal hydroxide. As for the counter electrode 10, MnO2 or NiO (OH) or PbO2 or ZnO, which is supported on a porous carbon paper by means of a PTFE binder, is used. By a reaction such as

$$MnO_2 + 2H_2O + 2e^- \rightarrow Mn(OH)_2 + 2OH^-$$ (2)

$$MnO_2 + 2H^+ + 2e^- \rightarrow Mn(OH)_2$$ (3)

$$NiO(OH) + H^+ + e^- \rightarrow Ni(OH)_2$$ (4)

$$PbO_2 + 2H^+ + 2e^- \rightarrow PbO + H_2O$$ (5)

hydroxyl ion is generated at the counter electrode 10, or proton that is generated at the sensing electrode 8 is consumed.

The liquid electrolyte to be held in the separator 6 is an aqueous solution of an alkali metal hydroxide, particularly preferably, NaOH or KOH, or an aqueous solution of a water soluble salt having no deliquescence, or pure water. As to the concentration of the liquid electrolyte, that of an alkali elctrolyte such as an aqueous solution of KOH is, for example, from 0.01 to 1 M (mol/dm3), and more widely from 0.001 to 3 M, and 0.1 M when not specified particularly. In the case of aqueous solution of MgSO4 and the like, the concentration of the liquid electrolyte is, for example, 5 wt %. Salts having no deliquescence include hydrogen carbonates of alkali metals, carbonates of alkali metals, double salts such as magnesium ammonium sulfate and potassium magnesium sulfate, zinc chloride or ammonium chloride, mixtures of them, and sodium acetate.

Best Mode

FIG. 5 through FIG. 15 illustrate the best embodiment. When the measurement temperature is not specified, it is room temperature, and the separator is a polyamide separator (n/n+m+p)=1×10$^{-2}$), the liquid electrolyte is 0.1 M KOH, and the structure of the sensor is that of FIG. 3. In place of the polyamide separtor, when the PP resin separtor (n/n+m)=1×10$^{-2}$) was used, the characteristics at room temperature and −10° C. were comparable, however, the durability at 60° C.×95% RH was a little inferior to that of the polyamide separator. As to the water in the water reservoir, pure water was used, but comparable characteristics were obtained for gelated water (water content: 80 wt %) using silica particulates (primary particle size: 5 to 50 nm) as a gelling agent. The silica particulates were silica obtained by a dry method wherein a silica compound was decomposed in gas phase, and when water is added to them, they form three-dimensional networks of silica and get gelated. Each diagram indicates the outputs or the mean output of four to five gas sensors. The current between two electrodes was amplified and biased so that the output of 1 V was obtained in the normal clean air, and the resulting output was used as the sensor output. For FIGS. 9, 12, 13 and 15, the current between both the electrodes was used as the output.

As comparative examples, one using a separator of polyamide resin not sulfonated (FIG. 7 and FIG. 8), and one using a proton conductive membrane in place of the separator and the two proton conductive membranes above and beneath the separator (trade name PRIMEA, of GORE JAPAN: PRIMEA is a registered trademark) were used.

Figure 5:
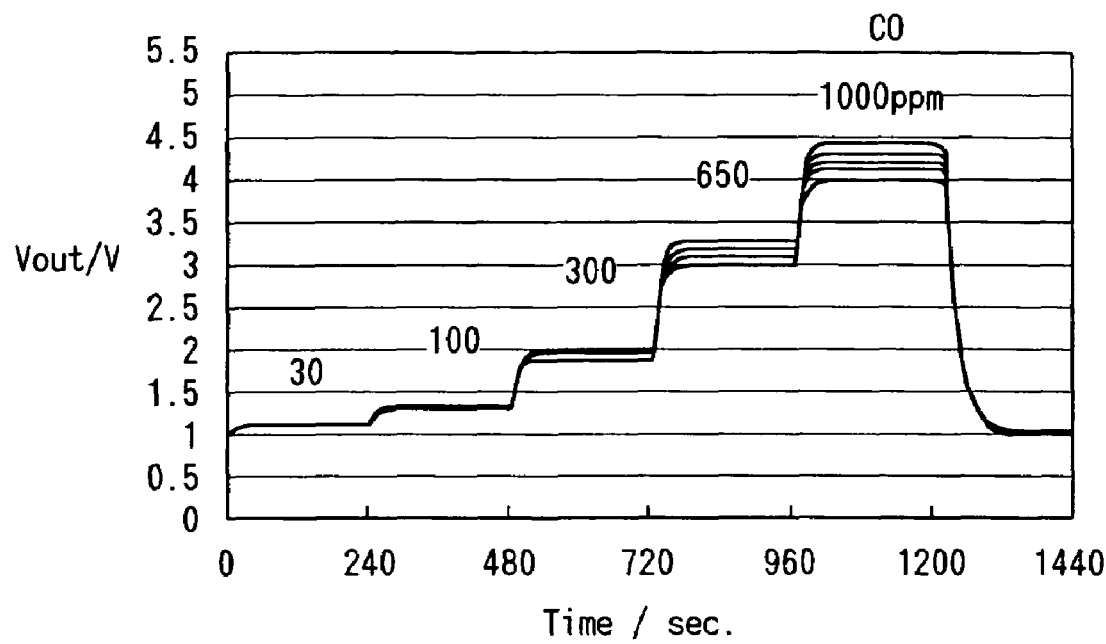
FIG. 5 is a characteristic diagram illustrating the responses to CO30-1000 ppm, at room temperature, of the gas sensors of the embodiment using a sulfonated separator.
Figure 6:
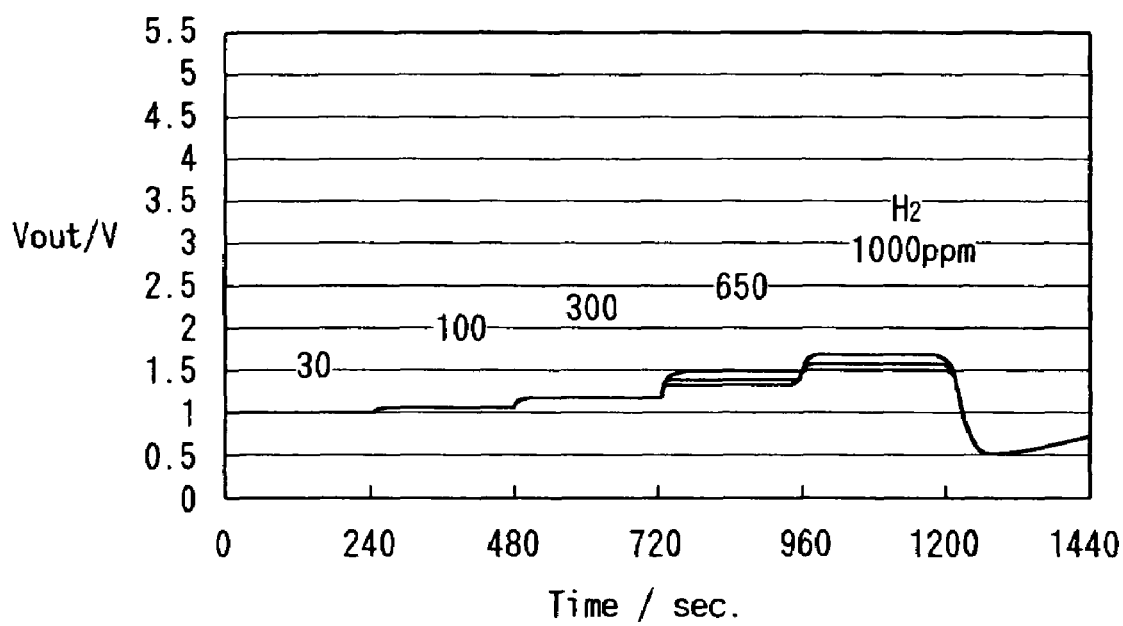
FIG. 6 is a characteristic diagram illustrating the responses to H2 30-1000 ppm at room temperature under the same conditions as FIG. 5.
Figure 7:
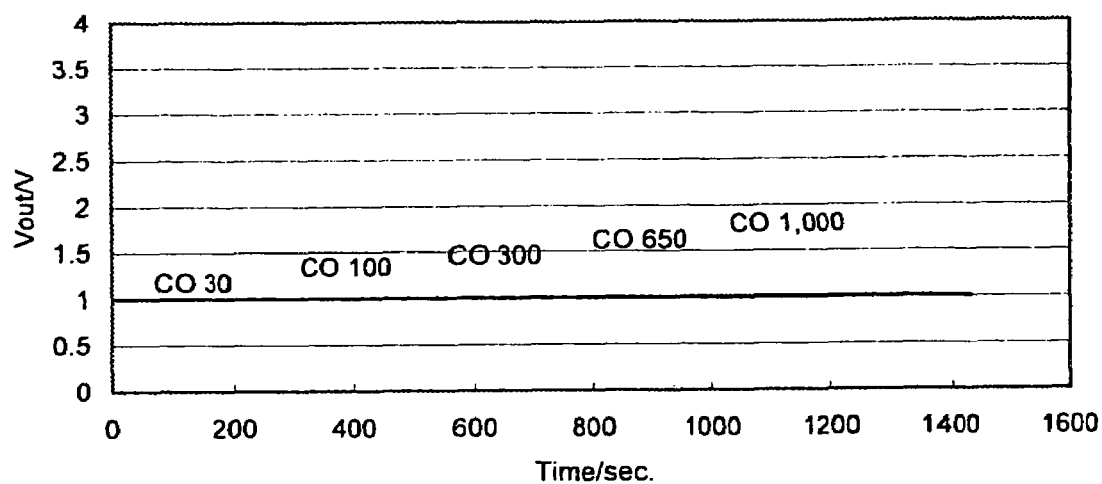
FIG. 7 is a characteristic diagram illustrating the responses to CO 30-1000 ppm, at room temperature, of a conventional sensor using a separator of low hydrophilicity.
Figure 8:
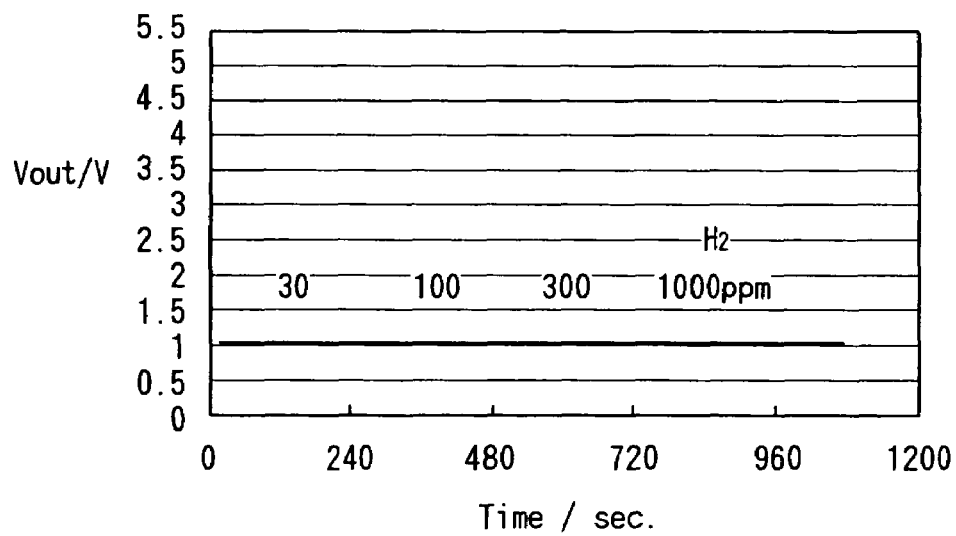
FIG. 8 is a characteristic diagram illustrating the responses to H2 30-1000 ppm, at room temperature, of a conventional sensor using a separator of low hydrophilicity.

When a separator that is not sulfonated and has a low hydrophilicity was used, no sensitivity was attained for CO or H2 (FIG. 7 and FIG. 8). When a sulfonated separator was used, sensitivity to CO and sensitivity to H2 were attained (FIG. 5 and FIG. 6). Such phenomena were not limited to the KOH liquid electrolyte. Similar phenomena were observed for the MgSO4 liquid electrolyte, and when pure water free of any electrolyte was held in the separator. As for the separator, similar characteristics were obtained for a polyvinyl alcoholic separator contains a large amount of alcoholic hydroxyl group, such as a copolymer of PTFE and vinyl alcohol. The emergence of sensitivity to gas with the increase in hydrophilicity of the separator is attributed to the formation of continuous channels of the liquid electrolyte with the increase in hydrophilicity.

Figure 9:
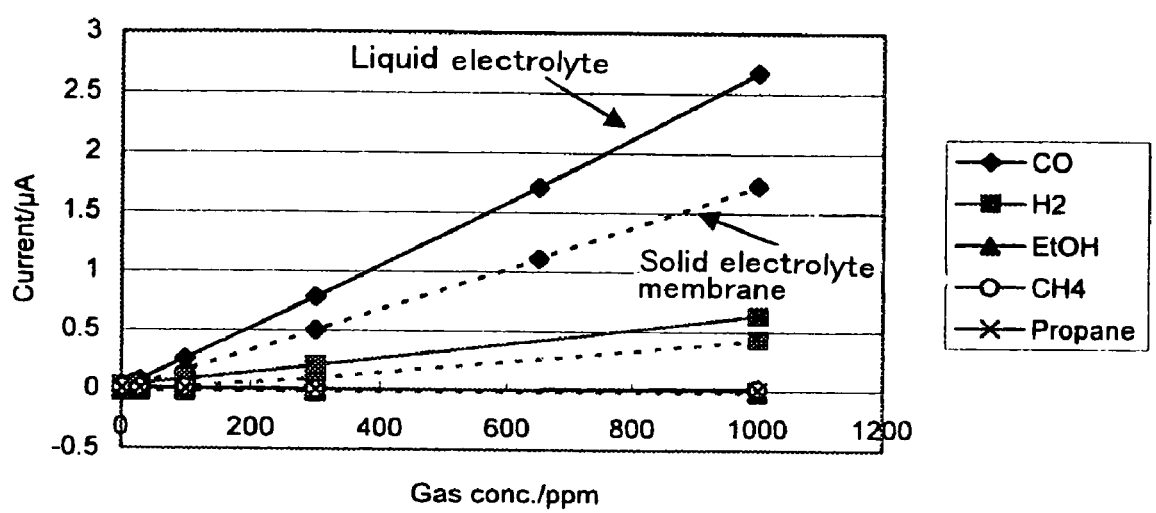
FIG. 9 is a characteristic diagram illustrating the response currents of a conventional gas sensor using a solid proton conductive electrolyte and the embodiment using a sulfonated separator holding KOH aqueous solution.

FIG. 9 illustrates sensitivities of gas sensors using solid electrolyte membrane and gas sensors using liquid electrolyte. The sensitivities obtained by the liquid electrolyte were higher than those obtained by the solid electrolyte. In the diagram, lack of sensitivity to EtOH (ethanol) or propane is due to the adsorption by the filter. No sensitivity to methane was attained even when the filter was not used.

Figure 10:
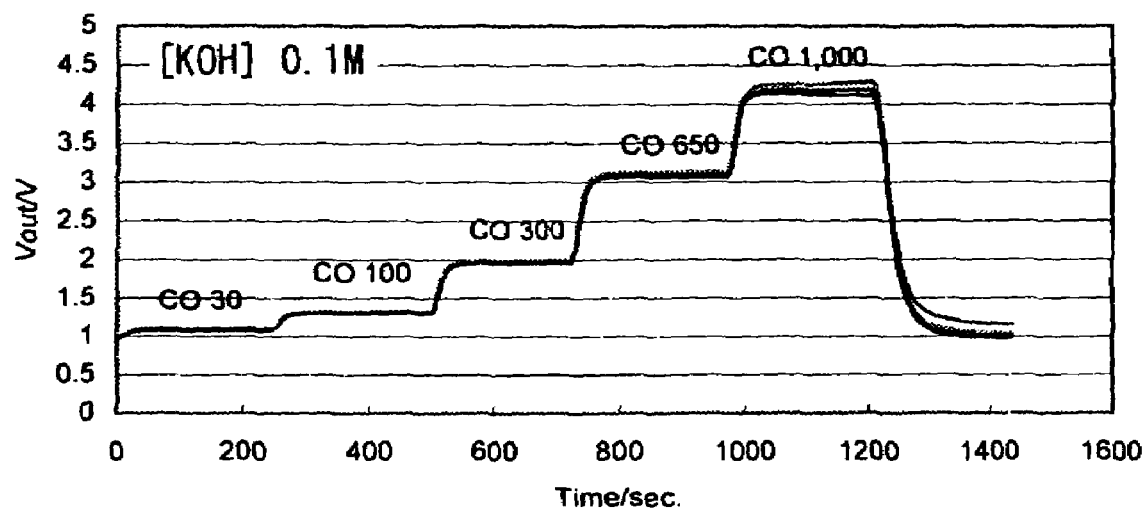
FIG. 10 is a characteristic diagram illustrating the responses to CO of the embodiment using 0.1M KOH aqueous solution.
Figure 11:
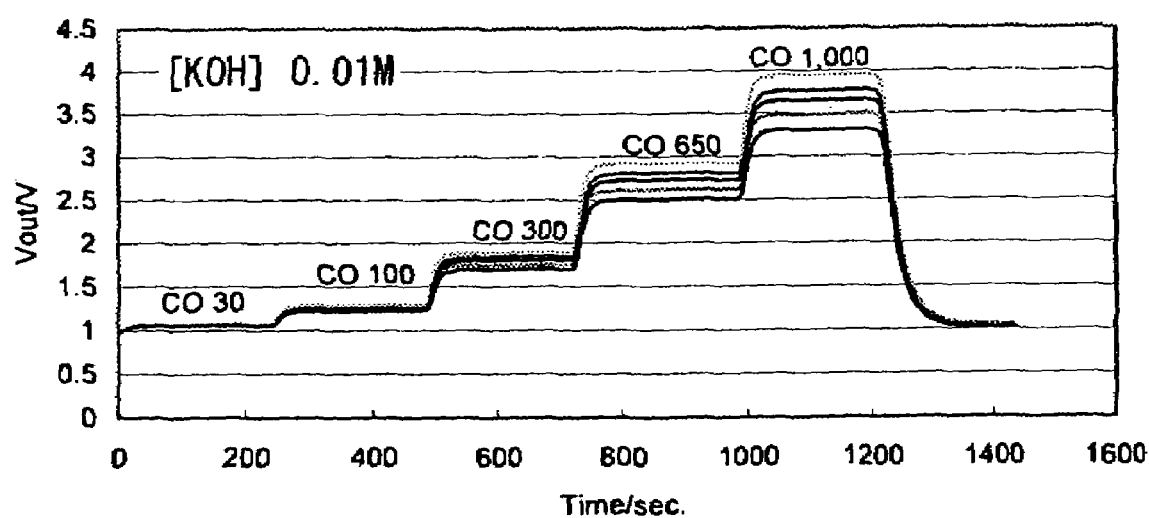
FIG. 11 is a characteristic diagram illustrating the responses to CO of the embodiment using 0.01M KOH aqueous solution.

FIG. 10 illustrates CO sensitivity with 0.1M KOH, and FIG. 11 illustrates CO sensitivity with 0.01M KOH. The sensitivity with 0.1M KOH was a little higher than the sensitivity with 0.01M KOH, and the dispersion of the sensitivity was smaller. Preferable concentration of KOH is from 0.01M to 3M. A part of KOH is considered to have been changed into potassium hydrogen carbonate by reaction with CO2 in air, but no effects on the characteristics were observed.

Figure 12:
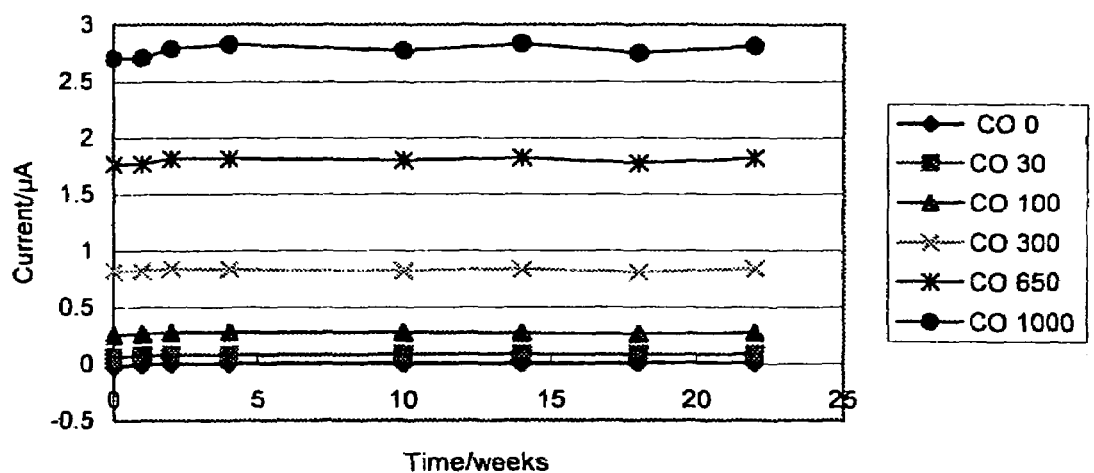
FIG. 12 is a characteristic diagram illustrating the characteristics of the gas sensor of the embodiment for 22 weeks.

FIG. 12 illustrates changes in characteristics over time at room temperature. The outputs were stable for 22 weeks.

Figure 13:
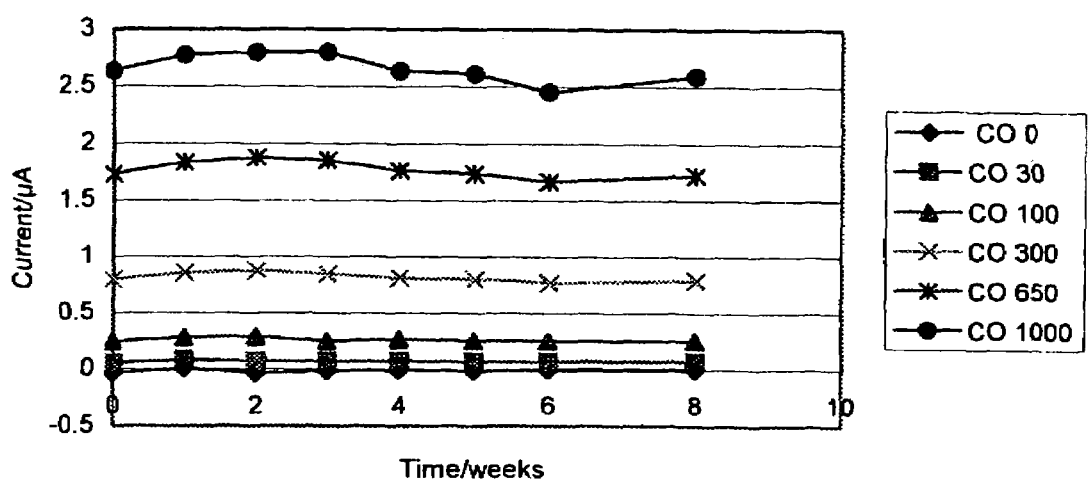
FIG. 13 is a characteristic diagram illustrating the durability performance of the gas sensor of the embodiment in an atmosphere of high temperature and high humidity (60° C.×95% RH).

FIG. 13 illustrates the results of CO sensitivity measurement at room temperature. Gas sensors were subjected to aging in an atmosphere of 60° C. and 95% RH for eight weeks, and the gas sensors were taken out of an aging chamber every week and subjected to the measurement. No deterioration was observed after the aging at 60° C. and 95% RH.

Figure 14:
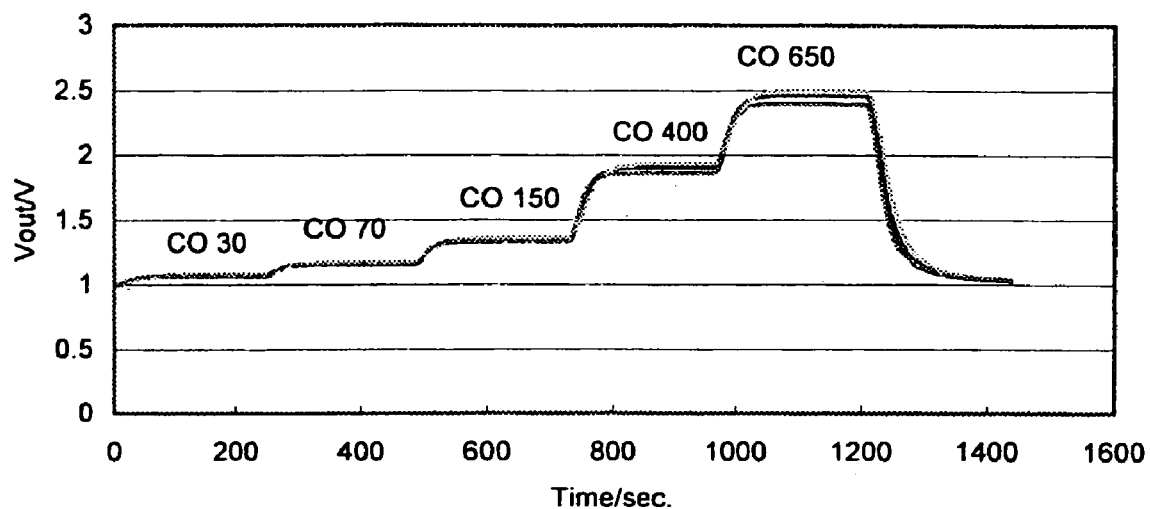
FIG. 14 is a characteristic diagram illustrating the responses to CO of the gas sensor of the embodiment at −10° C.

FIG. 14 illustrates the CO sensitivity at −10° C., and CO was successfully detected at this temperature.

Figure 15:
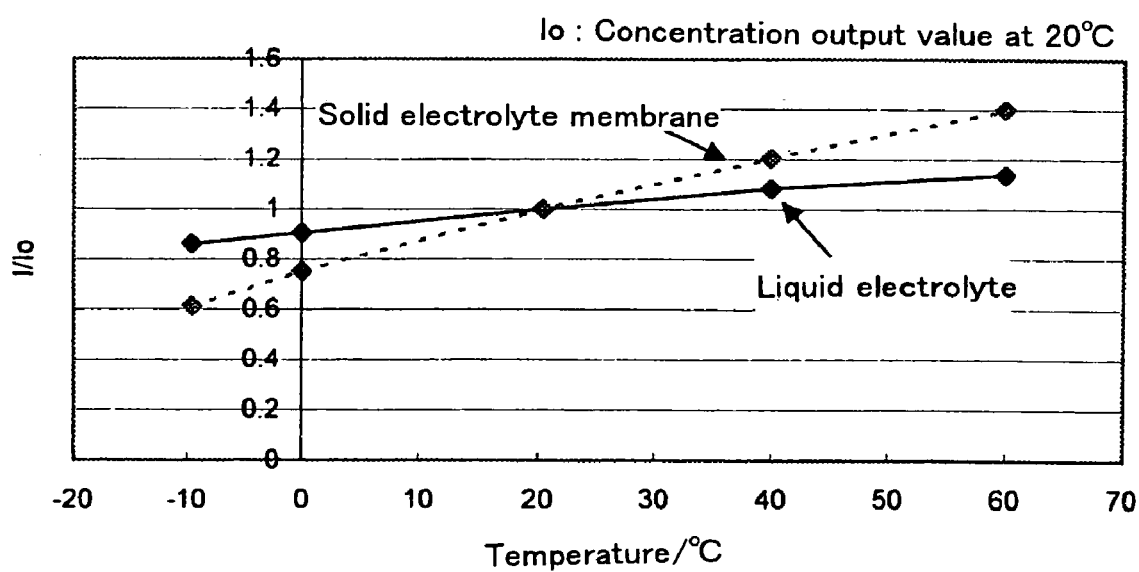
FIG. 15 is a characteristic diagram illustrating the ambient temperature dependencies of the gas sensor of the prior art using solid proton conductive electrolyte and the gas sensor of the embodiment.

FIG. 15 illustrates temperature dependencies of the comparative example using a proton conductive membrane and the embodiment using liquid electrolyte. The standard Io is the output current at 20° C. The temperature dependency of the embodiment was smaller. The separator using liquid electrolyte has a higher resistance than that of the proton conductive membrane, however, it is considered that the temperature dependency of the mobility of ions is smaller.

Embodiments Using Gelated Water

Embodiments using gelated water are illustrated in FIG. 16 through FIG. 23. In these embodiments, in place of a hydrophobic conductive membrane, a carbon paper of low hydrophobicity was used on the counter electrode side. No adhesive ring nor sealing material were used, and the metal can and the gasket were insulated by the gasket. The separator was a sulfonated PP separator. In the course of obtaining the data of FIG. 16 through FIG. 23, a variety of organic polymers were used as separators. There were separators having gas sensitivity and those having no gas sensitivity (FIG. 7 and FIG. 8). At first, the cause was unknown, however, it was found that presence or absence of ion exchange group such as sulfonic acid group is the cause. After that, moreover, it was found that comparable characteristics can be obtained by separators having, in place of sulfonic acid group, alcoholic hydroxyl group such as polyvinl alcohol group, and in turn, it was found that presence or absence of gas sensitivity is determined by the degree of hydrophilicity of the separator. Furthermore, it was found that a level of hydrophilicity that is obtained by surface treatment with a surface-active agent is not adequate and that the polymer itself must include a hydrophilic group.

As for particulates of silica, silica particulates that were obtained by hydrolyzing SiCl4 or the like in gas phase were used. The particle diameter of these particulates was from about 5 to 50 nm, and the particulates were spherical, their bulk density in dry condition was from about 50 to 100 g/dm3, and their specific surface area was about 200 m2/g. Water was added to these silica particulates and the mixture was mixed, while being subjected to shearing forces, by, for example, an ultramixer of MIZUHO INDUSTRIAL Co., LTD. During this time, the networks of the silica particulates were broken and their apparent particle diameter was reduced to 10-100 μm and including, for example, those of 1 μm or under. After mixing, when the mixture was left to stand, it gelated due to thixotropy. Due to being kept to stand, the apparent mean particle diameter of the gelling agent increased again to 10 μm or over. This indicates that chains of silica particulates were broken by mixing, then when being left to stand, their chains grew again to form three-dimensional network. It is considered that inside the newly formed networks, namely, in spaces between chains and chains of silica, liquid water is retained.

The resulting gel was stable and was not solated even when it was left to stand. The gel as it is or the gel that was cut into desired forms such as columns or cubes was stored in the metal can 28. The composition of the gel is, for example, 20 wt % of dry silica particulates and 80 wt % of water. The gel composition is preferably 10 to 30 wt % of the gelling agent, and more preferably, from 18 to 25 wt % of the gelling agent, and the balance is water.

A variety of gelated waters were evaluated. Polyacrylic acid was used as a gelling agent of synthetic polymers, and carrageenan (polysaccharide made from starch) was used as a gelling agent of natural polymers. Water of five times in weight of the gelling agent was added and gelated. In the embodiment, silica particulates of the dry method were used, and they were gelated by adding water of four times in weight of the gelling agent. Gels using these gelling agents were set in water reservoirs 33 and the gas sensors 2 were kept at 70° C. for one week. The shapes of gels using polyacrylic acid or carrageenan collapsed after one week, and gels stuck to the vicinity of the water vapor introducing hole 30, and the sensitivity to CO decreased. In contrast to them, the shape of the gel 34 of the embodiment did not change, no adhesion of the gel to the washer 28 was observed, and no changes in gas concentration characteristics in relation to CO were observed.

In the case of a natural polymer gelling agent such as carrageenan, when the gel was touched by fingers and then left to stand at room temperature for a week, growth of miscellaneous bacteria was found all over the gel. In contrast to it, in the case of the gel using silica particulates as its gelling agent, when it was touched by fingers and then left to stand, miscellaneous bacteria grew only on those areas touched, and bacteria did not spread to the remaining areas. This means that when inorganic particulates are used as a gelling agent, as energy sources for miscellaneous bacteria are not contained in it, bacteria can not grow. Accordingly, there is no need of adding an antiseptic agent to a gelling agent using inorganic particulates.

Characteristics when KOH Electrolyte and a Counter Electrode of MnO2 were Used

Figure 16:
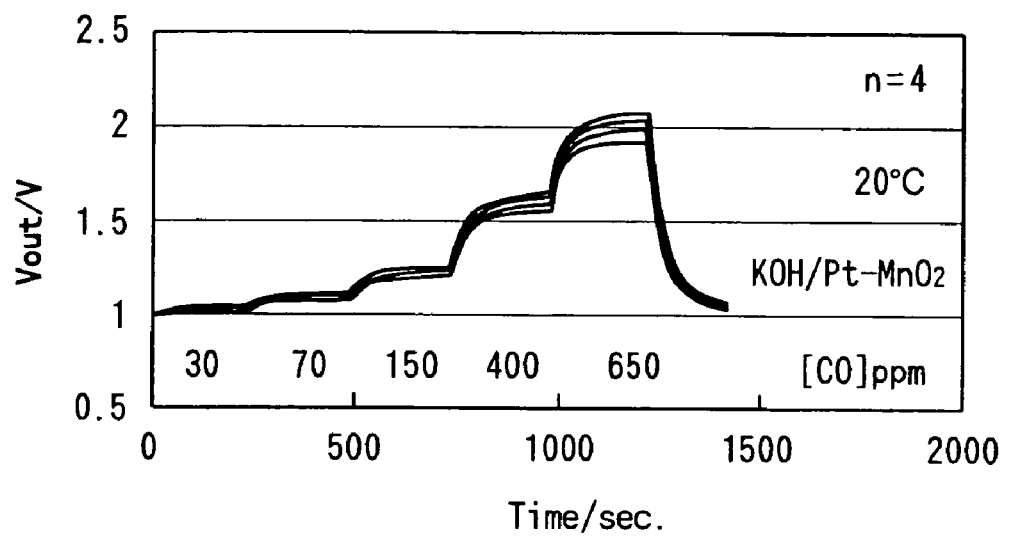
FIG. 16 is a characteristic diagram of a KOH/Pt—MnO2 system at 20° C.

FIG. 16 illustrates the characteristics of sensors wherein KOH aqueous solution of 1 M concentration was used as the liquid electrolyte, the sensing electrode was Pt catalyst supported by carbon black impregnated with Nafion solution (Nafion is a registered trademark of DuPont of solid polymer proton conductor), and the counter electrode was MnO2 supported by carbon paper. The number n of sensors was 4, and the measurement temperature was 20° C.

Characteristics when MgSO4 Electrolyte was Used

FIG. 17 through FIG. 23 illustrate characteristics when 5 wt % MgSO4 aqueous solution was used as the electrolyte. The sensing electrode and the counter electrode were Pt carried on carbon black impregnated with Nafion solution. However, in FIG. 17 and FIG. 23, the counter electrode was MnO2 supported in carbon paper. The ratio of the total weight of carbon black and Pt of the sensing electrode and the dry weight of Nafion thereof was from about 4:1 to 5:1. The number n of sensors was illustrated, and the measurement temperature was 20° C. except FIG. 20 through FIG. 22. The current between the sensing electrode and the counter electrode was amplified to provide the output voltage, and a bias was applied so that the output was 1 V when the sensor was in pure air. The bias and the gain of the amplifying circuit were common to all diagrams. The gas to be measured was CO or the like. The electrolyte may be ZnCl2 or ZnCl2+NH4Cl or the like.

Figure 17:
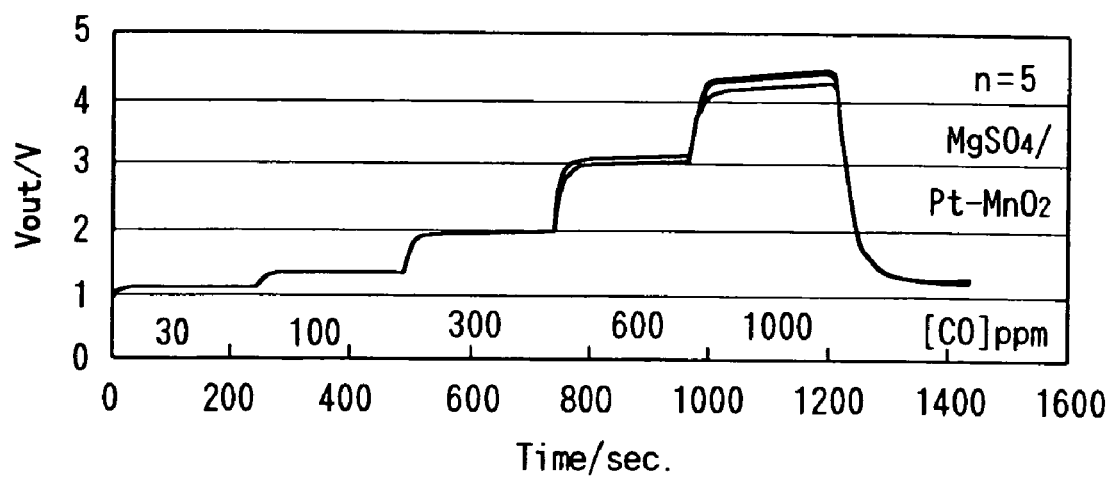
FIG. 17 is a characteristic diagram illustrating the responses to a variety of CO concentrations of an MgSO4/Pt—MnO2 system.
Figure 18:
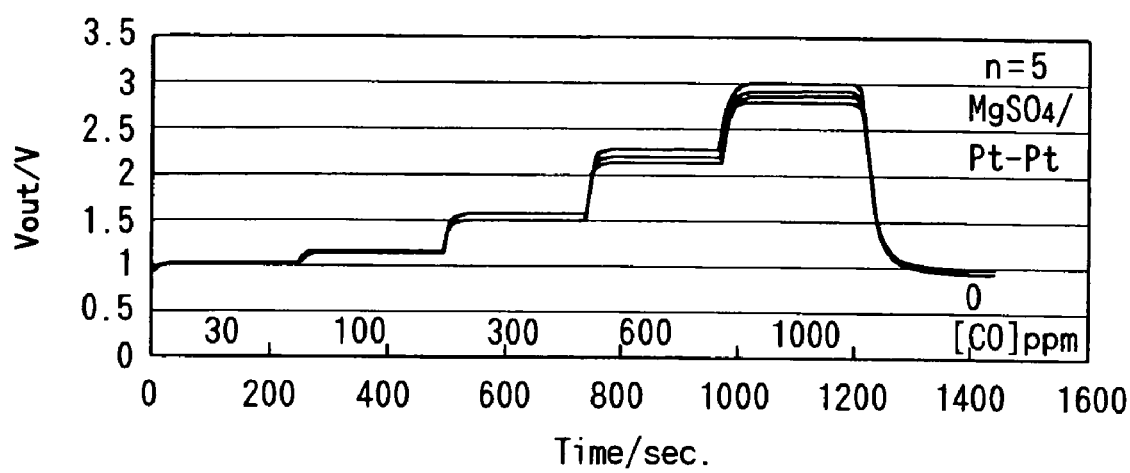
FIG. 18 is a characteristic diagram illustrating the responses to a variety of CO concentrations of an MgSO4/Pt—Pt system.

In FIG. 17, the counter electrode is MnO2, and in FIG. 18, the counter electrode is Pt. In case of the MnO2 counter electrode, the sensitivity obtained was higher than of the Pt counter electrode. When PbO2 or NiO(OH) was used as the counter electrode, the sensitivity was generally higher than that of a counter electrode using Pt catalyst.

Figure 19:
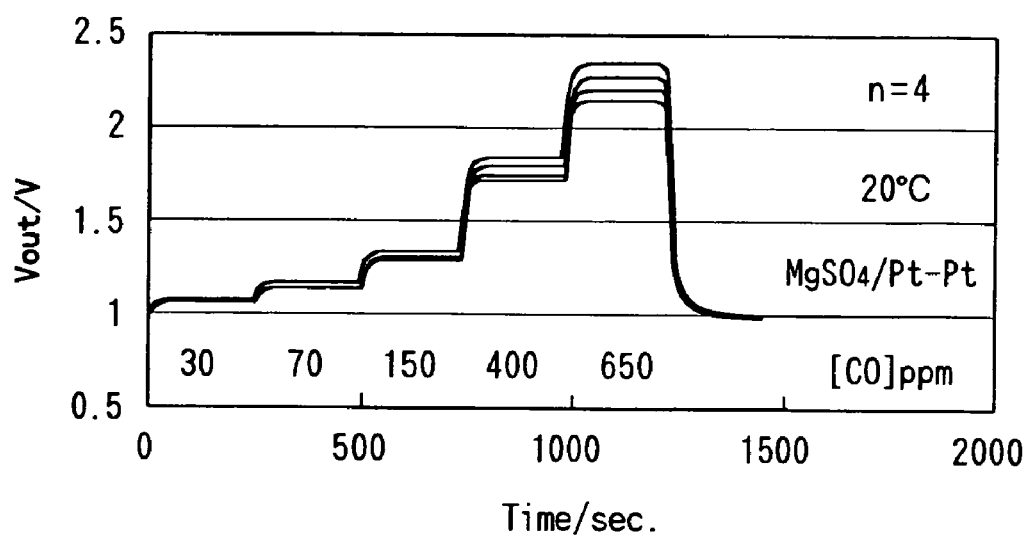
FIG. 19 is a characteristic diagram of the MgSO4/Pt—Pt system at 20° C.
Figure 20:
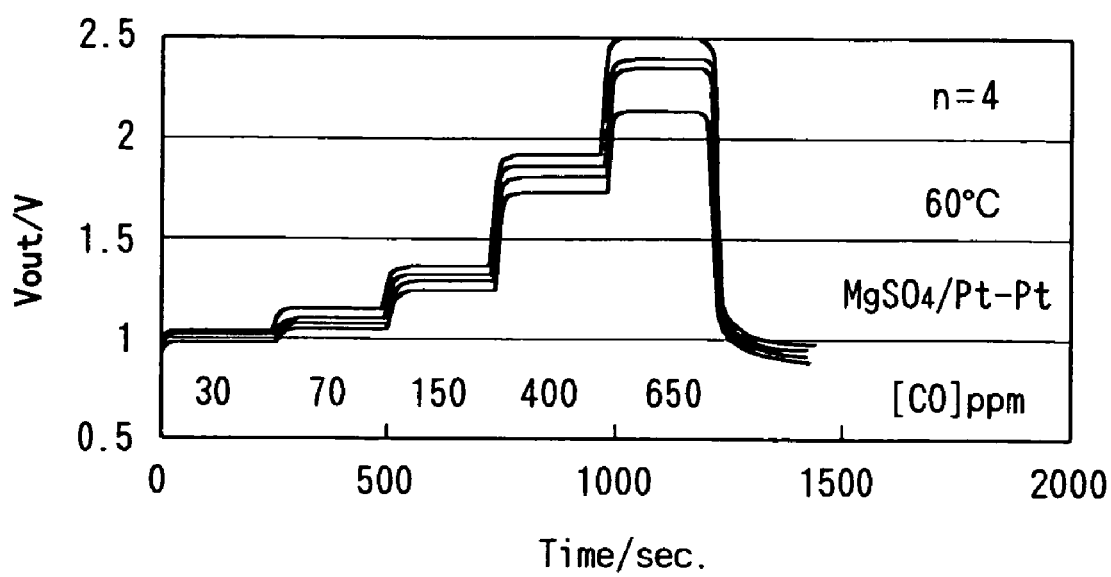
FIG. 20 is a characteristic diagram of the MgSO4/Pt—Pt system at 60° C.
Figure 21:
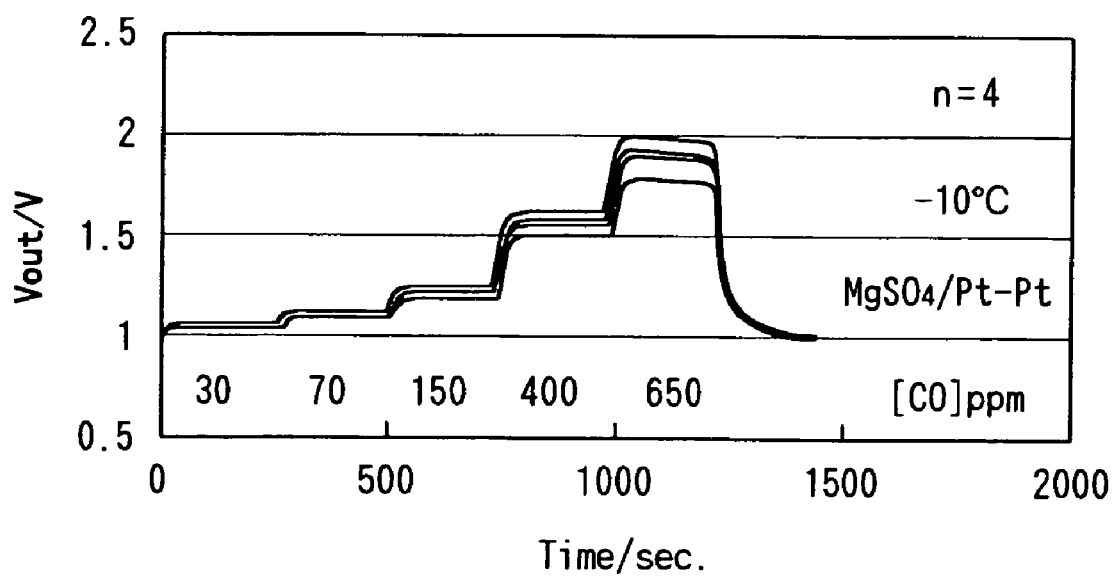
FIG. 21 is a characteristic diagram of the MgSO4/Pt—Pt system at −10° C.

FIG. 19 through FIG. 21 illustrate the dependency on the ambient temperature. The number n of sensors is 4, and the measurement temperatures are of three kinds, namely, 20° C., 60° C. and −10° C. The temperature dependency is small and is within a range that can be easily compensated by a thermistor or the like, and this was also the case when MnO2 was used in the counter electrode.

Thermal Endurance Against High Temperature

Figure 22:
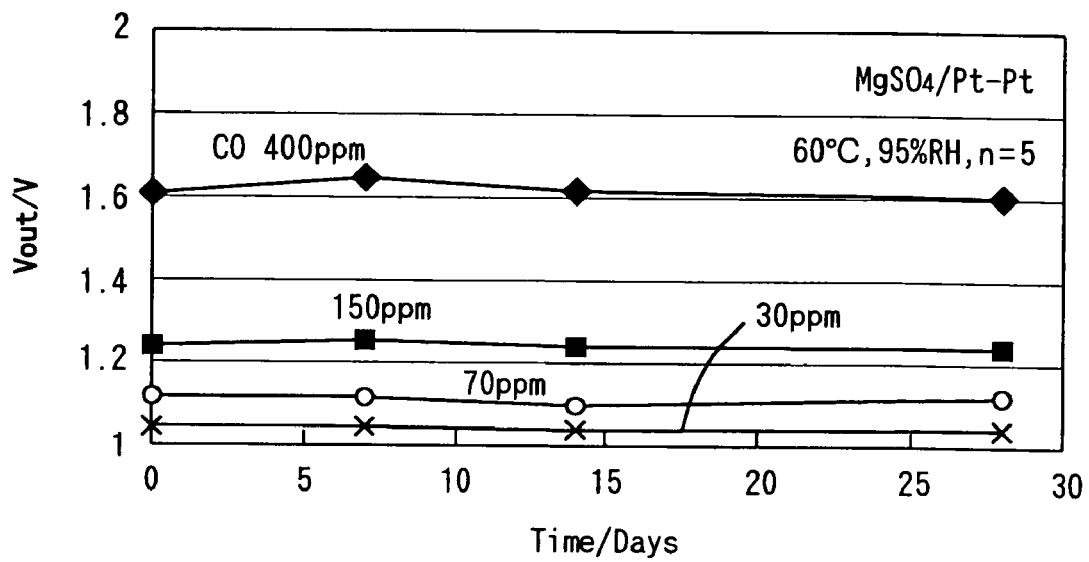
FIG. 22 is a characteristic diagram of the MgSO4/Pt—Pt gas sensor when the gas sensor was stored at 60° C. and 95% of relative humidity.

FIG. 22 illustrates characteristics to high temperature and high humidity experience, when the electrolyte was MgSO4 of 5 wt % concentration, and Pt catalyst supported on carbon black impregnated with Nafion solution was used in both the sensing electrode and the counter electrode. Five sensors were kept in an atmosphere of 60° C. and 95% RH, and when the sensors were to be measured, they were put back into an atmosphere of 20° C. and an ordinary humidity at the time of measurement, and the outputs to the respective gas concentrations were measured. Variations in sensor outputs even after four weeks of aging in the atmosphere of 60° C. and 95% RH were slight. FIG. 22 illustrates the case of the Pt counter electrode, but the case of the MnO2 counter electrode was similar.

Figure 23:
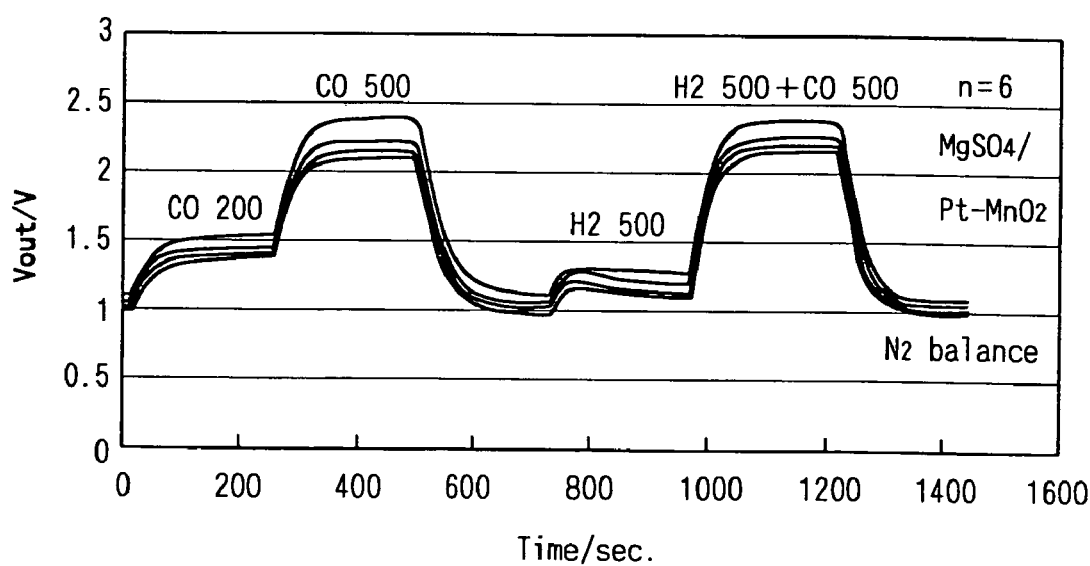
FIG. 23 is a characteristic diagram illustrating the response characteristics of the MgSO4/Pt—MnO2 gas sensor to CO in H2.

FIG. 23 illustrates the relative sensitivities to hydrogen and to CO when 5 wt % MgSO4 aqueous solution was used as the electrolyte, Pt supported on carbon black impregnated with Nafion solution was used as the sensing electrode, and MnO2 was used as the counter electrode. The gas component other than hydrogen and CO was N2. The sensitivity to CO to that to hydrogen is extremely high, and as MnO2 is used as the counter electrode, CO in hydrogen can be detected even in an atmosphere lacking oxygen. When CO in hydrogen is to be detected, to prevent poisoning of the sensing electrode, it is desirable to use a catalyst containing ruthenium oxide, such as Pt—RuO2 as the catalyst of the sensing electrode.

Detection of CO in Hydrogen

Figure 24:
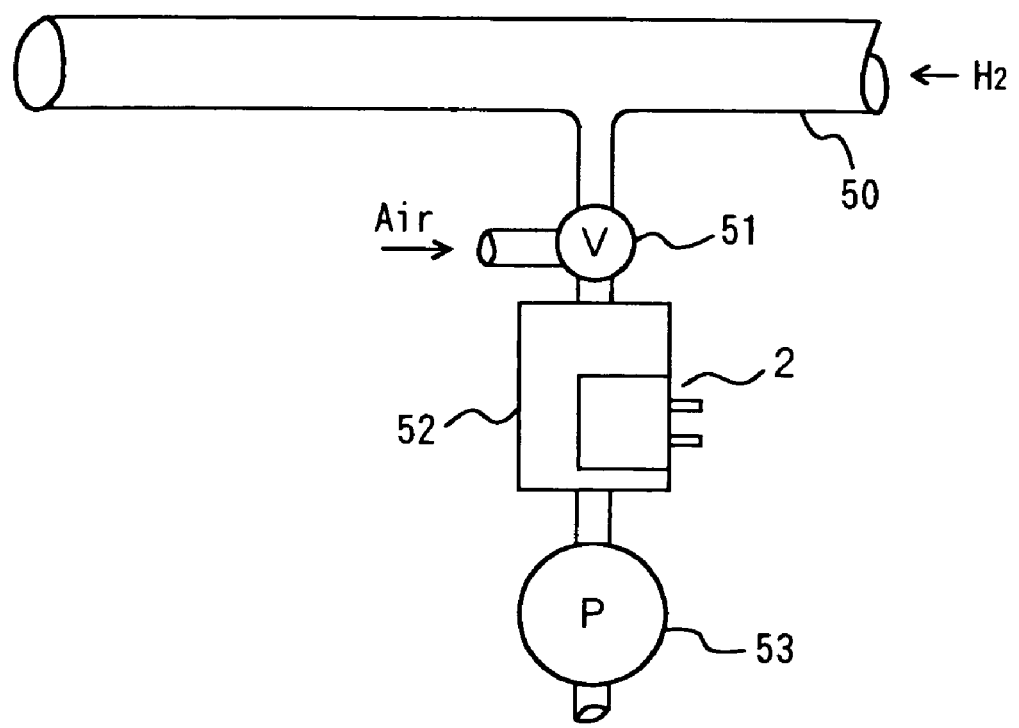
FIG. 24 is a diagram illustrating the layout of a device for measuring CO in hydrogen.

FIG. 24 illustrates a structure for detecting CO in hydrogen. 50 denotes a hydrogen tube that is a pipe for supplying hydrogen in a fuel cell or the like. The atmosphere can be switched between ambient air and hydrogen by means of a valve 51. A gas sensor 2 is placed in a test room 52, and a gas to be detected is sucked in by a suction pump 53. Hydrogen is sucked in intermittently to measure the CO concentration in hydrogen, and when the measurement is over, air or oxygen is introduced through the valve 51 to eliminate CO that is accumulated in the sensing electrode. FIG. 23 and FIG. 24 illustrate measurement of CO in hydrogen, but detection in CO or a combustible gas in nitrogen can be done similarly.

The invention claimed is:

1. A liquid electrochemical gas sensor comprising a porous separator, a sensing electrode, a counter electrode, and a water reservoir, said separator containing a liquid electrolyte, connected at least the sensing electrode and the counter electrode, and supplied water vapor from the water reservoir,
said separator being a hydrophilic organic polymer and supporting at least one of water, an aqueous solution of an alkali metal hydroxide, and an aqueous solution of a water soluble salt being not deliquescent, and
a solid electrolyte membrane interposed between the separator and the sensing electrode.

2. The liquid electrochemical gas sensor according to claim 1, said separator supporting at least one of the aqueous solution of the alkali metal hydroxide and pure water, and said gas sensor being for detecting a reducing gas.

3. The liquid electrochemical gas sensor according to claim 2, said separator supporting the aqueous solution of the alkali metal hydroxide.

4. The liquid electrochemical gas sensor according to claim 1, the counter electrode being an oxide or hydroxide of at least an element of a group consisting of Mn, Ni, Pb, and Zn.

5. The liquid electrochemical gas sensor according to claim 1, further comprising:
a metal can having an opening and a bottom; and a metal washer having an opening,
the metal can being provided with a narrowing part between the opening and the bottom,
the metal washer being supported by the narrowing part,
at least the counter electrode; the separator, and the sensing electrode being arranged on the metal washer, and
said water reservoir being a space between the metal washer and the bottom within the metal can.

6. The liquid electrochemical gas sensor according to claim 1, said gas sensor being for detecting CO in hydrogen gas or a reducing gas in an inert gas.

7. The liquid electrochemical gas sensor according to claim 1, further comprising a second solid electrolyte membrane which is interposed between the separator and the counter electrode.

8. The liquid electrochemical gas sensor according to claim 1, wherein the gas sensor is wickless and the separator, the sensing electrode and the counter electrode comprise an assembly, with a hydrophobic conductive membrane located between the water reservoir and the assembly and serving to block any liquid water from the water reservoir from reaching the assembly.

9. A liquid electrochemical gas sensor comprising a porous separator, a sensing electrode, a counter electrode, and a water reservoir, said separator containing a liquid electrolyte, connected at least the sensing electrode and the counter electrode, and supplied water vapor from the water reservoir, said separator being a hydrophilic organic polymer and supporting at least one of water, an aqueous solution of an alkali metal hydroxide, and an aqueous solution of a water soluble salt being not deliquescent, and a solid electrolyte membrane interposed at at least one location selected from the group consisting of between the separator and the sensing electrode and between the separator and the counter electrode.

10. The liquid electrochemical gas sensor according to claim 9, wherein the solid electrolyte membrane is interposed between the separator and the counter electrode.

11. The liquid electrochemical gas sensor according to claim 10, said separator supporting at least one of the aqueous solution of the alkali metal hydroxide and pure water, and said gas sensor being for detecting a reducing gas.

12. The liquid electrochemical gas sensor according to claim 11, said separator supporting the aqueous solution of the alkali metal hydroxide.

13. The liquid electrochemical gas sensor according to claim 10, the counter electrode being an oxide or hydroxide of at least an element of a group consisting of Mn, Ni, Pb, and Zn.

14. The liquid electrochemical gas sensor according to claim 10, further comprising:
a metal can having an opening and a bottom; and
a metal washer having an opening,
the metal can being provided with a narrowing part between the opening and the bottom,
the metal washer being supported by the narrowing part, at least the counter electrode, the separator, and the sensing electrode being arranged on the metal washer, and
said water reservoir being a space between the metal washer and the bottom within the metal can.

15. The liquid electrochemical gas sensor according to claim 10, said sensor being for detecting CO in hydrogen gas or a reducing gas in an inert gas.

16. The liquid electrochemical gas sensor according to claim 10, wherein the gas sensor is wickless and the separator, the sensing electrode and the counter electrode comprise an assembly, with a hydrophobic conductive membrane located between the water reservoir and the assembly and serving to block any liquid water from the water reservoir from reaching the assembly.

17. A liquid electrochemical gas sensor comprising a porous separator, a sensing electrode, a counter electrode, and a water reservoir, said separator containing a liquid electrolyte, connected at least the sensing electrode and the counter electrode, and supplied water vapor from the water reservoir, said separator being a hydrophilic organic polymer and supporting at least one of water, an aqueous solution of an alkali metal hydroxide, and an aqueous solution of a water soluble salt being not deliquescent, wherein the gas sensor is wickless and the separator, the sensing electrode and the counter electrode comprise an assembly, with a hydrophobic conductive membrane located between the water reservoir and the assembly and serving to block any liquid water from the water reservoir from reaching the assembly.

* * * * *